US00PP29045P3

(12) United States Plant Patent
Hooijman

(10) Patent No.: US PP29,045 P3
(45) Date of Patent: Mar. 6, 2018

(54) ROSE PLANT NAMED 'ESM R186'

(50) Latin Name: *Rosa hybrida*
Varietal Denomination: ESM R186

(71) Applicant: ESMERALDA BREEDING B.V., Aalsmeer (NL)

(72) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 82 days.

(21) Appl. No.: 14/998,736

(22) Filed: Feb. 9, 2016

(65) Prior Publication Data

US 2017/0231130 P1 Aug. 10, 2017

(51) Int. Cl.
*A01H 5/02* (2006.01)

(52) U.S. Cl.
USPC ..... Plt./144

(58) Field of Classification Search
USPC ..... Plt./144
See application file for complete search history.

(56) References Cited

PUBLICATIONS

UPOV hit on Rose plant 'ESM R186', QZ PBR 44338, published Dec. 15, 2014.*

* cited by examiner

*Primary Examiner* — Anne M Grunberg
(74) *Attorney, Agent, or Firm* — C. A. Whealy

(57) ABSTRACT

A new and distinct cultivar of Rose plant named 'ESM R186', characterized by its upright and strong flowering stems; moderately vigorous to vigorous growth habit and high productivity; dark green-colored leaves; relatively tall flower buds; creamy white and greenish white colored flowers that are held on strong pedicels on relatively large sprays; freely flowering habit with typically about six flowers per spray and good productivity with about twelve flowering stems per plant produced per year; and excellent postproduction longevity.

1 Drawing Sheet

Botanical designation: *Rosa hybrida.*
Cultivar denomination: 'ESM R186'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R186'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in October, 2009 of a proprietary Rose selection identified as Line 363, not patented, as the female, or seed, parent with a proprietary Rose selection identified as Line 462, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in November, 2010.

Asexual reproduction of the new Rose plant by bud grafting in El Quinche, Pichincha, Ecuador since December, 2010 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R186'. These characteristics in combination distinguish 'ESM R186' as a new and distinct Rose plant:

1. Upright and strong flowering stems.
2. Moderately vigorous to vigorous growth habit and high productivity.
3. Dark green-colored leaves.
4. Relatively tall flower buds.
5. Creamy white and greenish white-colored flowers that are held on strong pedicels on relatively large sprays.
6. Freely flowering habit with typically about six flowers per spray and good productivity with about twelve flowering stems per plant produced per year.
7. Excellent postproduction longevity.

Plants of the new Rose differ from plants of the female parent selection in the following characteristics:

1. Plants of the new Rose are more vigorous than plants of the female parent selection.
2. Flowers of plants of the new Rose have more petals than flowers of plants of the female parent selection.

Plants of the new Rose differ from plants of the male parent selection in the following characteristics:

1. Plants of the new Rose are slightly shorter than plants of the male parent selection.

2. Plants of the new Rose have more flowers per spray than plants of the male parent selection.

Plants of the new Rose can be compared to plants of *Rosa hybrida* 'Peach Vision', not patented. In side-by-side comparisons conducted in El Quinche, Pichincha, Ecuador, plants of the new Rose differed from plants of 'Peach Vision' in the following characteristics:

1. Plants of the new Rose were more vigorous than plants of 'Peach Vision'.
2. Leaves and terminal leaflets of plants of the new Rose were longer than leaves and terminal leaflets of plants of 'Peach Vision'.
3. Petal margins of plants of the new Rose were more undulate than petal margins of plants of 'Peach Vision'.
4. Flowers of plants of the new Rose had more petals than flowers of plants of 'Peach Vision'.
5. Cut flowers of plants of the new Rose lasted about four days longer than cut flowers of plants of 'Peach Vision'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the upper left of the sheet is a side perspective of a typical flowering stem of 'ESM R186' and the photograph at the bottom left of the sheet is a close up view of a typical flowering stem of 'ESM R186'.

The photograph at the upper right of the sheet is a close-up view of a typical developed flower of 'ESM R186'.

The photographs at the lower right of the sheet are close-up views of the upper and lower surfaces of typical leaves of 'ESM R186'.

DETAILED BOTANICAL DESCRIPTION

The aforementioned photographs, following observations and measurements describe plants grown in 10-liter containers in a polyethylene-covered greenhouse in El Quinche, Pichincha, Ecuador and under typical hydroponic Rose production practices. Plants were pinched 13 to 14 weeks after planting and were 46 weeks old when the photographs were taken and 109 weeks old when the description was taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'ESM R186'.

Parentage:

*Female, or seed, parent.*—Proprietary seedling selection of *Rosa hybrida* identified Line 363, not patented.

*Male, or pollen, parent.*—Proprietary seedling selection of *Rosa hybrida* identified Line 462, not patented.

Propagation:

*Type.*—By bud grafting.

*Time to initiate roots, summer.*—About 15 days at temperatures about 26° C. to 30° C.

*Time to produce a rooted young plant, summer.*—About 30 days at temperatures about 22° C. to 26° C.

*Root description.*—Thick, fibrous; close to N199B and 200D in color.

*Rooting habit.*—Moderately freely branching; dense.

Plant description:

*Plant and growth habit.*—Perennial shrub; upright and strong flowering stems; typically grown as a spray-type cut flower; moderately vigorous to vigorous growth habit.

*Productivity.*—Plants of the new Rose are highly productive with about 12.72 flowering stems developing per plant per year.

*Plant height.*—About 120 cm.

*Plant width (spread).*—About 65 cm.

*Lateral branches.*—Quantity: Freely branching habit with about 16 lateral branches developing per plant. Length: About 87 cm. Diameter: About 6.9 mm. Internode length: About 5.4 cm. Texture: Smooth, glabrous; older stems, woody. Strength: Moderately strong to strong. Color: Close to 146A and N199A. Thorns: Density: Sparse. Shape: Triangular with sharp acuminate apices. Height: About 7.3 mm. Length, at base: About 5.6 mm. Color, immature: Close to 176A. Color, mature: Close to 177B and N199C.

Leaf description:

*Arrangement.*—Alternate; compound with typically seven leaflets per leaf.

*Leaf length.*—About 18.9 cm.

*Leaf width.*—About 11 cm.

*Terminal leaflet length.*—About 7 cm.

*Terminal leaflet width.*—About 4.4 cm.

*Lateral leaflet length.*—About 4.8 cm.

*Lateral leaflet width.*—About 3.2 cm.

*Leaflet shape.*—Ovate.

*Leaflet apex.*—Acute.

*Leaflet base.*—Short attenuate.

*Leaflet margin.*—Serrate.

*Leaflet texture, upper and lower surfaces.*—Smooth, glabrous; papery to coriaceous.

*Leaflet venation pattern.*—Pinnate.

*Leaflet color.*—Developing leaflets, upper surface: Close to 137A. Developing leaflets, lower surface: Close to 146B. Fully expanded leaflets, upper surface: Close to 139A; venation, close to between 146D and 146A. Fully expanded leaflets, lower surface: Close to 147B; venation, close to 146C.

*Petioles, leaves.*—Length: About 1.7 cm. Diameter: About 2 mm. Texture, upper and lower surfaces: Smooth, glabrous. Color, upper surface: Close to 146A to 146C. Color, lower surface: Close to between 146B and 144B.

*Petioles, leaflets.*—Length: About 2.2 cm. Diameter: About 1.3 mm. Texture, upper surface: Prickly. Texture, lower surface: Smooth, glabrous. Color, upper surface: Close to 146A to 146D. Color, lower surface: Close to 146D.

*Stipules.*—Arrangement and appearance: Two, adnate to the petiole, leafy in appearance. Length: About 3 cm. Width: About 3.3 mm. Shape: Roughly deltoid. Apex: Acuminate, tapered. Base: Tapered. Margin: Entire. Texture, upper and lower surfaces: Smooth;

membranous. Venation pattern: Pinnate. Color, upper and lower surfaces: Close to 146A.

Flower description:

*Flower type and arrangement.*—Symmetrical rosette flowers; flowers typically grown as spray-types; flowers face upright; freely flowering with typically six flowers per spray.

*Flowering season.*—Plants of the new Rose flower year-round under greenhouse conditions; early flowering habit, plants begin flowering about 77 days after pinching.

*Spray diameter.*—About 16.6 cm.

*Spray height.*—About 20 cm.

*Flower diameter.*—About 7.2 cm.

*Flower depth* (*height*).—About 3.7 cm.

*Flower longevity.*—Excellent postproduction longevity; flowers maintain good substance for about 32 to 34 days on the plant and for about 16 days as a cut flower; flowers persistent.

*Fragrance.*—Slightly fragrant.

*Flower buds.*—Rate of opening: About 21 to 23 days. Length: About 3.5 cm. Diameter: About 2.7 cm. Shape: Ovoid. Color: Close to 144A.

*Petals.*—Quantity: About 49 per flower; petals imbricate. Length: About 3.6 cm. Width: About 3.4 cm. Shape: Nearly round. Apex: Blunt to short acute. Base: Obtuse. Margin: Entire, undulate. Texture, upper and lower surfaces: Smooth, glabrous; papery to coriaceous. Color: When opening, upper surface: Close to between 27C and 157A; towards the base, close to 1C. When opening, lower surface: Close to between 27C and 157B; towards the base, close to 1C. Fully opened, upper surface: Close to between N155C and 157A; towards the base, close to 157C. Fully opened, lower surface: Close to between N155C and 155C; towards the base, close to 157A.

*Petaloids.*—Quantity: About eleven; whorled. Length: Variable. Width: Variable. Shape: Irregularly shaped. Apex: Blunt to short acute. Base: Obtuse. Margin: Mostly uneven. Texture, upper and lower surfaces: Smooth, glabrous; papery to coriaceous. Color: When opening, upper and lower surfaces: Close to 155C and 56C. Fully opened, upper and lower surfaces: Close to 155C and 56B.

*Sepals.*—Quantity per flower: Typically five in a single whorl. Length: About 3.6 cm. Width: About 1.1 cm. Shape: Roughly deltoid. Apex: Tapered. Base: Truncate. Margin: Entire; ciliate and/or glandular. Texture, upper and lower surfaces: Leathery. Color: When opening, upper surface: Close to 146B and 145B. When opening, lower surface: Close to 146A and N144C. Fully opened, upper surface: Close to 146A and 144C. Fully opened, lower surface: Center, close to 166C; towards the apex, close to 146A; towards the base, close to 144B.

*Pedicels.*—Length: About 3.3 cm. Diameter: About 3.5 mm. Strength: Strong. Angle: About 33° from vertical. Texture: Glandular. Color: Close to 144A.

*Reproductive organs.*—Stamens: Quantity: About 126 per flower. Anther length: About 2.3 mm. Anther shape: Reniform. Anther color: Close to N163C and 162A. Filament color: Close to 157A. Pollen amount: Abundant. Pollen color: Close to 163A. Pistils: Quantity: About 120 per flower. Pistil length: About 1.4 cm. Stigma shape: Broadly reniform. Stigma color: Close to 161A. Style length: About 9 mm. Style color: Close to 157C and 185C. Receptacle height: About 9 mm. Receptacle diameter: About 8.5 mm. Receptacle shape: Cup-shaped. Receptacle texture: Smooth, glabrous. Receptacle color: Close to 144A. Fruits: Length: About 2.9 cm. Diameter: About 1.7 cm. Texture: Smooth. Color: Close to N172C and 146B. Seeds: Quantity per fruit: About ten. Length: About 5 mm. Diameter: About 4 mm. Texture: Smooth. Color: Close to 162C.

Pathogen & pest tolerance: Plants of the new Rose have been observed to have good tolerance to Powdery Mildew, Downy Mildew and *Botrytis*. Plants of the new Rose have not been observed to be tolerant to pests and other pathogens common to Rose plants.

Temperature tolerance: Plants of the new Rose have been observed to tolerate temperatures ranging from 0° C. to 35° C.

It is claimed:

1. A new and distinct Rose plant named 'ESM R186' as illustrated and described.

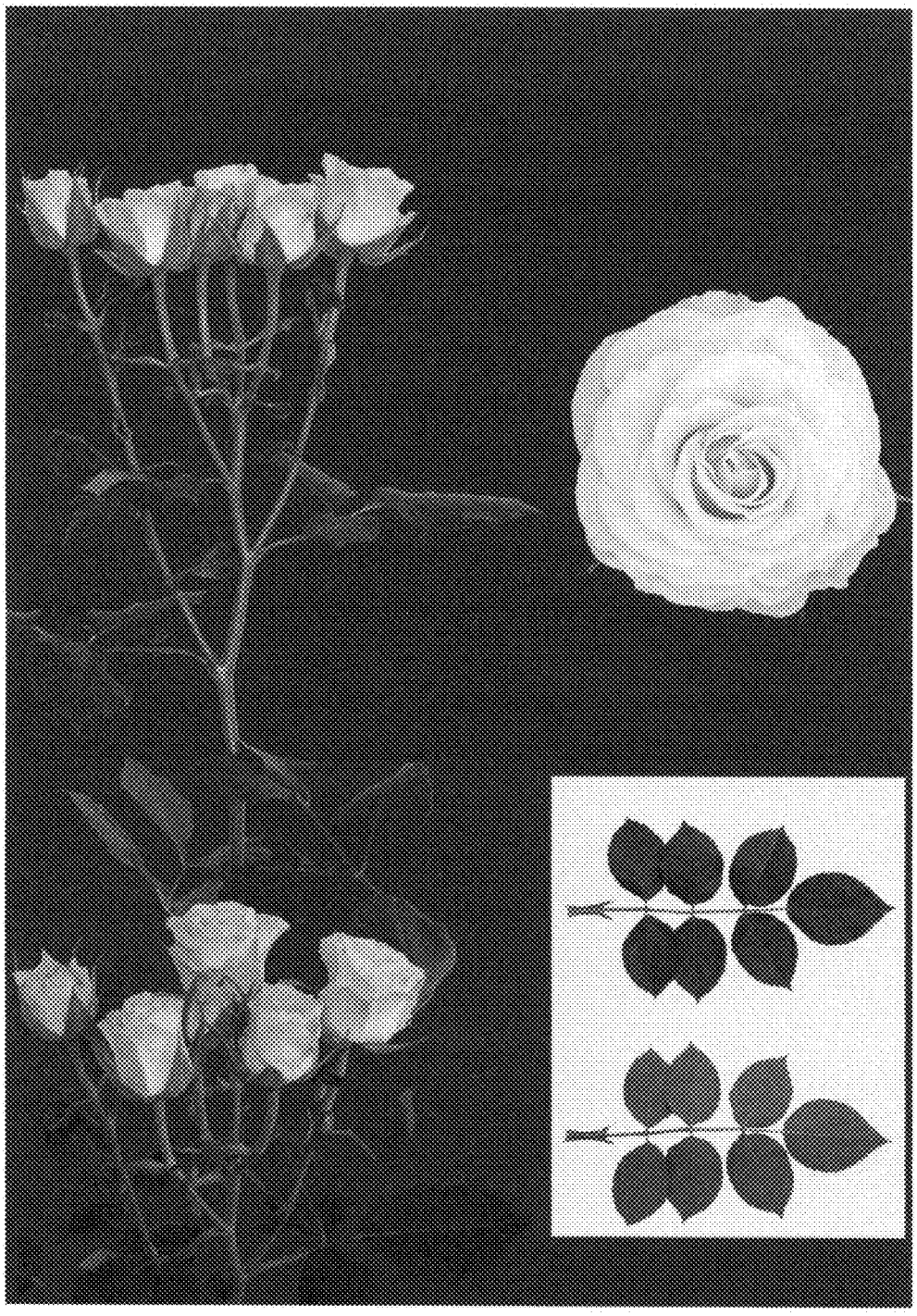

* * * * *